United States Patent [19]

Dias et al.

[11] Patent Number: 4,482,834
[45] Date of Patent: Nov. 13, 1984

[54] ACOUSTIC IMAGING TRANSDUCER

[75] Inventors: J. Fleming Dias; H. Edward Karrer; John D. Larson, III; David A. Wilson, all of Palo Alto, Calif.; Amin M. Hanafy, Andover, Mass.

[73] Assignee: Hewlett-Packard Company, Palo Alto, Calif.

[21] Appl. No.: 52,705

[22] Filed: Jun. 28, 1979

[51] Int. Cl.³ .............................................. H01L 41/08
[52] U.S. Cl. ................................... 310/327; 310/334; 310/336
[58] Field of Search .................. 310/334–337, 310/327; 73/632, 642, 644; 128/660

[56] References Cited

U.S. PATENT DOCUMENTS

| | | | |
|---|---|---|---|
| 2,881,336 | 4/1959 | Elion | 310/327 |
| 2,943,297 | 6/1960 | Steinberger et al. | 310/337 X |
| 3,189,767 | 6/1965 | Goldman et al. | 310/327 |
| 3,716,828 | 2/1973 | Massa | 310/337 X |
| 3,952,387 | 4/1976 | Iinuma et al. | 310/334 X |
| 4,101,795 | 7/1978 | Fukumoto et al. | 310/336 |
| 4,211,948 | 7/1980 | Smith et al. | 310/334 X |
| 4,217,516 | 8/1980 | Iinuma et al. | 310/335 |
| 4,217,684 | 8/1980 | Brisken et al. | 310/334 X |

Primary Examiner—Mark O. Budd
Attorney, Agent, or Firm—Edward Y. Wong; F. D. LaRiviere

[57] ABSTRACT

The acoustic imaging transducer described herein incorporates an acoustic stack contained in an alumina housing which also provides structure for electrically connecting the transducer array elements to system signal processing electronics.

14 Claims, 5 Drawing Figures

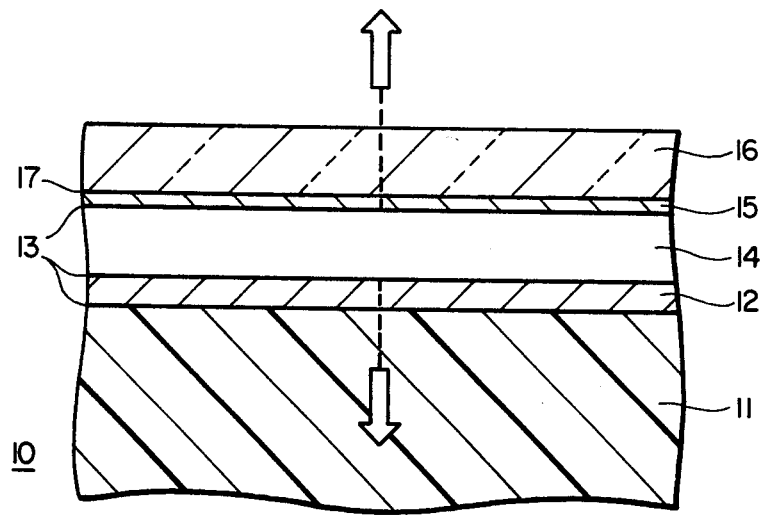
FIG__1
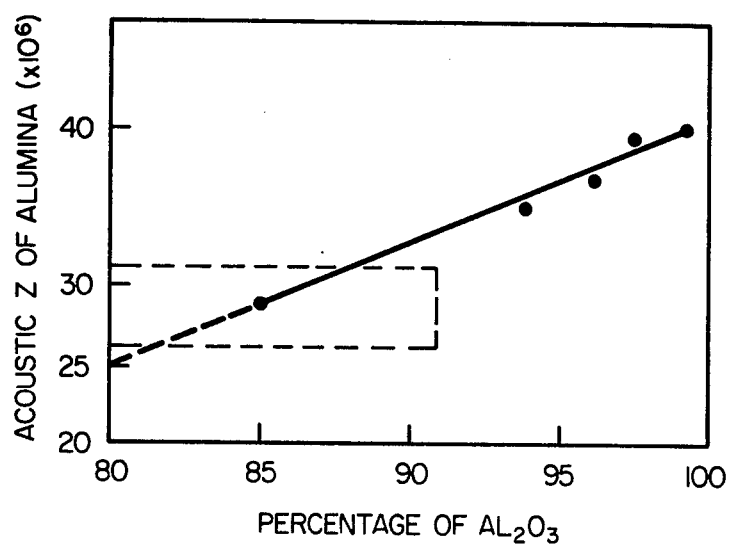
FIG__2

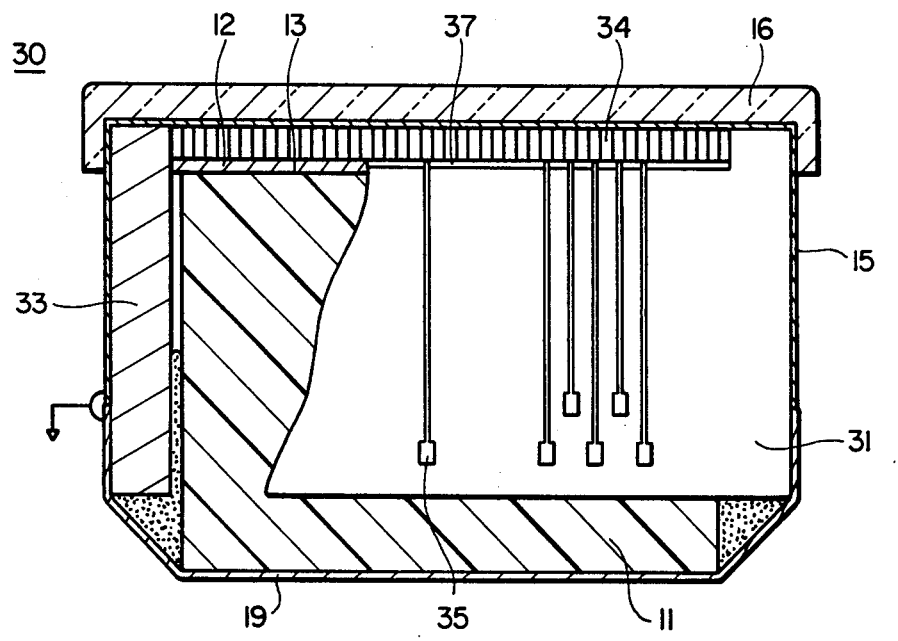
FIG_3
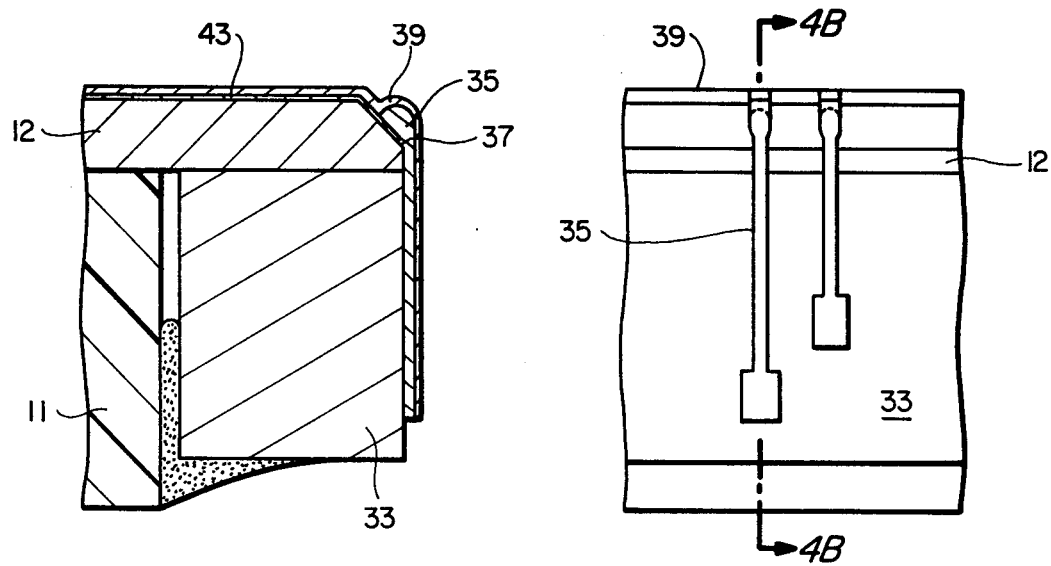
FIG_4B  FIG_4A

ACOUSTIC IMAGING TRANSDUCER

BACKGROUND AND SUMMARY OF THE INVENTION

An acoustic imaging transducer typically consists of an array of piezoelectric elements disposed on a planar surface for radiating and receiving acoustic waves in a direction normal to that surface. By properly phasing these elements, the beam can be focused at a predetermined distance and scanned azimuthally. The elements being bilateral in function, two beams are generated in diametrically opposite directions. In general, to obtain good depth resolution, one of the beams must be absorbed and its energy dissipated in some form of an acoustic absorber.

An acoustic absorber should have an acoustic impedance that substantially matches the acoustic impedance of the piezoelectric elements, and typically comprises heavy metal particles such as tungsten sintered in a thermoplastic binder such as polyvinyl/chloride. Because the absorber (hereinafter also referred to as "backing") is electrically conductive, an intermediate layer of a non-conducting material must be inserted between the elements and the backing. The layers of material form a stack, each one of which must be acoustically matched to achieve maximum transfer of acoustic energy across the interfaces.

An acoustic transducer constructed according to the principles of the present invention comprises a tungsten-vinyl backing to absorb the unwanted acoustic energy, an electroplated alumina substrate of proper acoustic impedance, an alumina housing to support the acoustic stack and to provide structure for electrically connecting the transducer array elements to the system signal processing electronics, an array of PZT elements, a grounding foil, and an acoustic lens.

DESCRIPTION OF THE DRAWING

FIG. 1 is a cross-sectional view of an acoustic stack constructed according to the preferred embodiment of the present invention.

FIG. 2 is a graph of the acoustic impedance of the substrate material used in the acoustic stack of FIG. 1 plotted as a function of the percentage of aluminum oxide.

FIG. 3 is a side cross-sectional view of an acoustic imaging transducer incorporating the acoustic stack of FIG. 1 according to the preferred embodiment of the present invention.

FIG. 4(a) is a side view of a detailed portion of the acoustic imaging transducer of FIG. 3.

FIG 4(b) is a cross-sectional view of the acoustic imaging transducer of FIG. 4(a) at A—A.

DESCRIPTION OF THE PREFERRED EMBODIMENT

Referring to FIG. 1, the construction of the tungsten-vinyl backing 11 of stack 10 is described in co-pending patent application Ser. No. 958,082 filed on Nov. 6, 1978, by John D. Larson, III, which is assigned to the assignee hereof, and incorporated by reference as if fully set forth herein. Backing 11 is prepared for bonding to alumina substrate 12 by shaving or otherwise removing excess vinyl and other surface debris to expose the maximum amount of tungsten to the alumina. One way of assuring maximum exposure of tungsten at the bonding surface of the backing is to remove surface material to a depth of about one-half the diameter of the largest tungsten particles sintered in the backing. After initial removal of material to the recommended depth, the surface of the backing is then lapped and polished smooth and flat to within ±0.5 μm.

Conventional methods of shaving the surface of the backing may loosen the tungsten particles or otherwise disturb the acoustic integrity of the backing. To avoid such damage, mylar paper impregnated with diamond dust may be used for the shaving and lapping process. Any other method of removing excess material from the bonding surface of the backing may be used so long as tungsten particles are not loosened or the acoustic integrity of the backing is not disturbed and the maximum amount of tungsten is exposed to the alumina.

By exposing as much tungsten as possible at the bonding surface, better acoustic match is achieved and transmission of acoustic energy into backing 11 from array 14 via substrate 12 is maximized. The improved acoustic match results in wider bandwidth and more uniform response by each element in the array. Greater exposure of the tungsten also provides rigid structural support for each element of the array when formed after remaining elements of the stack are bonded thereon.

The lapping process described above is applicable to acoustic absorbers constructed of other materials as well. If another binder is used rather than vinyl, or iron filings instead of tungsten powder, or any combination of these with other appropriate materials, improved performance can be achieved by the lapping process described above before assembly with other parts of the transducer.

Substrate 12 should be an electrical insulator which acoustically matches lead zirconate titanate (PZT), designated 14 in FIG. 1, on one side and tungsten-vinyl backing 11 on the other. A typical impedance required is around $25 \times 10^6$ rayls. One such alumina material having suitable properties is an alumina brick made by the Coors Porcelain Co. and referred to as AD85. AD85 bricks are used in the construction of high temperature furnaces, among other things. The graph in FIG. 2 shows acoustic impedance as a function of the percentage of aluminum oxide content. The darkened area is the range of characteristic impedance of AD85. The balance is made up of other oxides such as silica, magnesia, calcia which act as fluxing agents and are added to improve fabrication and firing characteristics. After the ceramic is fired in a kiln, the residue is mostly alumina and voids. The percentage of voids determines the proper impedance match to the other elements of the acoustic stack. Additional variations in acoustic impedance are obtainable by varying the firing time of the ceramic in the kiln.

For optimum acoustic match, the thickness of substrate 12 should be small compared to the wavelength of sound traveling in that material. Conversely, since substrate 12 contributes to the strength of the stack and since strength is related to the thickness of the substrate, it is also desirable that the substrate be as thick as possible. If the wavelength of sound in a material is given by $$\lambda = V/f$$

where V is the velocity and f is the frequency of the soundwave traveling therein, then materials in which sound energy travels with relatively high velocity are the most desirable. For a given frequency of sound, a substrate constructed of such materials may be thicker to provide strength without degrading the acoustic match it provides. Thus, alumina may be approximately twice as thick as a substrate constructed of glass or quartz.

Substrate 12, PZT layer 14, and brass foil 15 are bonded to backing 11 by epoxy layers as shown at 13. PZT layer 14 comprises lead titanate zirconate sandwiched between vacuum deposited layers of 500 Å chromium covered with 5000 Å of gold. PZT layer 14 is bonded to the plated surface of substrate 12 with conductive epoxy as shown in FIG. 1. To maximize the capacitance effect of the epoxy bond, that bond should be as thin as possible to assure that the capacitance of the PZT layer is the controlling electrical influence. Additionally, this and other epoxy bonds must be thin to assure acoustic matching and maximum transfer of acoustic energy.

Acoustic lens material 16 is then bonded to the brass foil 15 by silastic bond 17. Lens 16 may be integrally formed on foil 15 without silastic layer 17 prior to bonding the foil to PZT layer 14. Substrate 12 also includes a layer of conductive material, such as copper, which is not shown in FIG. 1 and described elsewhere in this specification.

Referring now to FIG. 3, acoustic imaging transducer 30 includes the elements of acoustic stack 10 housed in alumina housing 31 and having electrical conductors 35 formed thereon. Alumina housing 31, including side walls 33 thereof, forms a sturdy acoustic module to conveniently house backing 11 and support PZT array of elements, generally designated 34 herein, on substrate 12. It also provides the surface for silk-screened, thick-film conductors 35 for coupling PZT array 34 to the signal processing system.

As shown in FIGS. 4(a) and 4(b), substrate 12 and the silk-screened conductors 35, which are bent over beveled edge 37, are simultaneously electroplated with 0.5 to 0.8 mils of copper at 39 and flashed with 50 microinches of gold (Au). Copper (Cu) is used because it approximately matches both alumina and PZT acoustically. Electroplating 39 strengthens the interface connection of the thick film conductor 35 with the vacuum deposited Cr-Au 43 film at beveled edge 37 as shown in FIGS. 3, 4(a), and 4(b).

Prior to plating, substrate 12 is prepared by vacuum depositing a base layer of 500 Å of chromium (Cr) and 5000 Å of Au. The vacuum deposition layer connects thick film conductors 35 on the side of alumina housing 31 to Cr-Au film 43 on the alumina substrate. In so doing, each element of array 14 is individually connected to the thick film conductors 35, when the PZT layer 14 is sawed as described later in this specification.

The array of PZT elements 34 is formed by sawing PZT layer 14 and substrate 12 into a plurality of rectangular shaped elements. As described elsewhere in this specification, layer 14 is epoxied onto an alumina substrate 12. Electroplating 39 of substrate 12 is patterned to delineate each array element. Following this pattern, the PZT substrate is sawn through alumina substrate 12 to backing 11.

Grounding foil 15 couples one side of all elements of array 14 to ground. Since this side of the transducer typically faces the body of the patient, this grounding configuration is preferred to prevent the hazard of electrical shock. Foil 15 may be made from 0.8 mil copper or brass shim stock. Similarly, shield 19 may be constructed of the same or similar material and grounded in common with foil 15 as shown in FIG. 3.

Lens 16 collimates the acoustic beam to a predetermined distance along a plane that is orthogonal to the plane in which the dynamic focusing takes place. The lens, itself, can be formed of several commercially available materials—such as Sylgard 170, a product of Dow Corning Corporation. This material has an impedance that closely matches the human body and enables the lens to have the proper focal distance.

We claim:

1. An acoustic stack comprising:
   an acoustic absorber having at least one bonding surface for bonding materials thereto;
   strengthening a layer of insulating material bonded to the prepared surface of the absorber, the other surface of said strengthening insulating layer having a layer of electrically conductive material formed thereon;
   a layer of piezoelectric material bonded to the electrically conductive material formed on the strengthening insulating layer, said layer of piezoelectric material having layers of electrically conductive material formed on both surfaces thereof;
   a layer of electrically conductive material bonded to the other surface of the piezoelectric material; and
   a layer of material closely matching the acoustic impedance of the human body covering the third layer of electrically conductive material.

2. An acoustic stack as in claim 1 employed in an acoustic imaging transducer wherein:
   said layers of insulating and piezoelectric materials are formed into individual elements for radiating and detecting acoustic waves.

3. An acoustic stack as in claim 2 enclosed in means for housing the acoustic stack and for electrically connecting the individual elements to signal processing means.

4. An acoustic stack as in claim 1 or 2 wherein the insulating layer is constructed of a material in which acoustic energy travels with relatively high speed.

5. An acoustic stack as in claim 1 or 2 or 4 wherein the insulating layer is constructed of alumina.

6. An acoustic imaging transducer employing an acoustic stack comprising:
   an acoustic absorber having at least one bonding surface for bonding materials thereto;
   a strengthening layer of insulating material bonded to the prepared surface of the absorber, the other surface of said strengthening insulating layer having a layer of electrically conductive material formed thereon;
   a layer of piezoelectric material having first and second layers of electrically conductive material formed on the surfaces thereof, said first layer of conductive material being bonded to said other surface of the strengthening insulating layer;
   a third layer of electrically conductive material bonded to the second layer of conductive material on the piezoelectric material;
   a housing of insulating material bonded to said layer of insulating material for enclosing said acoustic absorber and layers of materials bonded thereto; and
   a layer of material closely matching the acoustic impedance of the human body covering the third layer of electrically conductive material;

said layers of insulating material and piezoelectric material being formed into a plurality of acoustic elements for radiating and receiving acoustic waves;

said housing having a plurality of electrical conductors formed thereon for connecting each of said elements to the signal processing system.

7. An acoustic imaging transducer as in claim 6 wherein the layers of conductive material on said other surface of the layer of insulating material is formed into separate electrical conductors for defining each of said pluralities of acoustic elements and for connecting said element to the electrical conductor on said housing.

8. An acoustic imaging transducer as in claim 6 or 7 wherein the insulating layer and the housing is constructed of a material in which acoustic energy travels with relatively high speed.

9. An acoustic imaging transducer as in claim 8 wherein the insulating layer and the housing is constructed of alumina.

10. An acoustic imaging transducer as in claim 1 or 6 wherein the acoustic absorber comprises particles of heavy metal sintered in a binder.

11. An acoustic imaging transducer as in claim 10 or 6 wherein excess material is removed from the bonding surface of the acoustic absorber to expose the maximum amount of heavy metal for bonding.

12. An acoustic imaging transducer as in claim 11 wherein excess material is removed from the bonding surface of the acoustic absorber to a depth of about one-half the diameter of the largest heavy metal particle sintered therein.

13. An acoustic imaging transducer as in claim 1 wherein the heavy metal particles are constructed of tungsten and the binder is vinyl.

14. An acoustic imaging transducer as in claim 6 further including a fourth layer of electrically conductive material bonded to the outer surface of the housing and electrically connected to third layer of electrically conductive material.

* * * * *

UNITED STATES PATENT AND TRADEMARK OFFICE
CERTIFICATE OF CORRECTION

PATENT NO. : 4,482,834

DATED : November 13, 1984

INVENTOR(S) : J. Fleming Dias et al.

It is certified that error appears in the above—identified patent and that said Letters Patent is hereby corrected as shown below:

Column 4, line 15, "strengthening a layer" should read -- a strengthening layer --

Signed and Sealed this

Ninth Day of April 1985

[SEAL]

Attest:

DONALD J. QUIGG

Attesting Officer

Acting Commissioner of Patents and Trademarks